US006918925B2

(12) United States Patent
Tehrani

(10) Patent No.: US 6,918,925 B2
(45) Date of Patent: Jul. 19, 2005

(54) BRANCHED AORTIC ARCH STENT GRAFT AND METHOD OF DEPLOYMENT

(76) Inventor: Hassan Tehrani, 227 Michigan Ave. #303, Miami Beach, FL (US) 33139

( * ) Notice: Subject to any disclaimer, the term of this patent is extended or adjusted under 35 U.S.C. 154(b) by 426 days.

(21) Appl. No.: 10/104,599

(22) Filed: Mar. 22, 2002

(65) Prior Publication Data

US 2002/0156518 A1 Oct. 24, 2002

Related U.S. Application Data

(60) Provisional application No. 60/278,139, filed on Mar. 23, 2001.

(51) Int. Cl.$^7$ .................................................. A61F 2/06
(52) U.S. Cl. .................... 623/1.11; 623/1.13; 623/1.23; 623/1.35
(58) Field of Search ............................. 623/1.11, 1.12, 623/1.23, 1.35

(56) References Cited

U.S. PATENT DOCUMENTS

| 5,984,955 | A | | 11/1999 | Wisselink ....................... 623/1 |
|---|---|---|---|---|
| 6,030,414 | A | | 2/2000 | Aheri ............................. 623/1 |
| 6,099,548 | A | * | 8/2000 | Taheri ....................... 623/1.11 |
| 6,187,033 | B1 | * | 2/2001 | Schmitt et al. ............. 623/1.35 |
| 6,197,049 | B1 | * | 3/2001 | Shaolian et al. ........... 623/1.35 |
| 6,641,606 | B2 | * | 11/2003 | Ouriel et al. ............... 623/1.12 |
| 6,682,537 | B2 | * | 1/2004 | Ouriel et al. ............... 606/108 |
| 2001/0003161 | A1 | | 6/2001 | Vardi et al. ................ 623/1.11 |
| 2001/0027338 | A1 | | 10/2001 | Gremberg .................. 623/1.13 |

FOREIGN PATENT DOCUMENTS

| WO | WO 98/19628 | 5/1998 |
|---|---|---|
| WO | WO 00/44309 | 8/2000 |

OTHER PUBLICATIONS

International Search Report in International (PCT) Application No. PCT/US02/08895 dated Aug. 21, 2002.

* cited by examiner

Primary Examiner—Julian W. Woo
Assistant Examiner—Sarah Webb
(74) Attorney, Agent, or Firm—Marshall, Gerstein & Borun LLP

(57) ABSTRACT

A stent-graft device for placement in the aortic arch comprises a graft having a main body sized for insertion in the aortic arch and defining a central lumen, the graft including a left branch and a right branch attached to the main body and arranged for flow communication with the central lumen, each of the main body, the left branch and the right branch including a stent and shiftable between a narrowed undeployed configuration and an expanded deployed configuration. The left and right branches each branch include a sheath arranged to constrain the branches in the undeployed configuration, and the left and right branches are arranged to be pulled into the left or right brachiocephalic artery exclusively under tension by respective pull wires. An inner sheath is arranged to constrain the main body of the graft in the undeployed configuration, and an outer sheath is arranged to constrain each of the left branch and the right branch in a folded position generally adjacent the main body when each of the left branch and the right branch is in the undeployed configuration.

20 Claims, 9 Drawing Sheets

BRANCHED AORTIC ARCH STENT GRAFT AND METHOD OF DEPLOYMENT

RELATED APPLICATIONS

This application claims priority under 35 U.S.C. § 119(e) from U.S. Provisional Application No. 60/278,139, filed Mar. 23, 2001.

FIELD OF THE INVENTION

The present invention relates to repair of aneurysms using vascular grafts and, more specifically, to a two-branch aortic graft used to treat aneurysms in the aortic arch.

BACKGROUND OF THE INVENTION

Aneurysms of the thoracic aorta occur relatively infrequently with an occurrence of 10.4 cases per 100,000 person years. For those patients having an untreated aneurysm, aneurysm rupture is the leading cause of death, aneurysm rupture having a mortality rate of 74–94%. The current standard of care for management of ascending and arch thoracic aneurysms greater than 5.5 cm diameter, and descending thoracic aneurysms greater than 6.5 cm diameter is surgery with prosthetic graft replacement. Because of the concomitant comorbidities associated in this group of patients, including coronary artery disease (30%), heart failure (14%), hypertension (72%) cerebrovascular disease (11%), and chronic obstructive airway disease (31%), many of these patients are excluded from being surgical candidates for aneurysm repair because of the prohibitive operative risk. Despite advances in peri-operative care and surgical techniques including the use of left heart bypass, hypothermic circulatory arrest and spinal cord drainage/cooling, the mortality and paraplegia rate may be as high as 35% and 21% respectively.

Advances in the field of endovascular therapy have led to the development of translumenal stent-grafts to treat thoracic aneurysmal disease. Some have demonstrated the feasibility of deploying stent-grafts to treat isolated descending thoracic aneurysms. However, aneurysms isolated to the descending thoracic comprise only 35% of the total, with aneurysms of the ascending aorta (40%), the arch aorta (15%), or mixed (10%) comprising the balance.

The devices currently being inserted are either individually custom made by the interventionalist or, are being investigated in company-sponsored Food and Drug Administration (FDA) trials, such as the Thoracic Excluder™ (W. L. Gore & Assoc.®) or the Talent™ (Medtronic®). The use of these devices is limited to the presence of satisfactory "landing zones" proximal and distal to the aneurysm sac allowing for a sufficient seal to exclude the aneurysm from the circulation. In patients with descending thoracic aneurysms with arch involvement, isolated arch aneurysms, or distal ascending thoracic aneurysms, little possibility currently exists for treatment using an endovascular approach because of the lack of a suitable side-branched stent-graft that can at the same time "straddle" and exclude the aneurysm while maintaining normal blood flow to the brachiocephalic vessels. To date, there are only limited occurrences of successful endovascular placement of triple-branched stent-graft completely across the aortic arch.

DETAILED DESCRIPTION OF THE PREFERRED EMBODIMENT

The embodiment described herein is not intended to be exhaustive or to limit the scope of the invention to the precise form or forms disclosed. Instead, the following embodiment has been described in order to best explain the principals of the invention and to enable others skilled in the art to follow its teachings.

Figure 1:
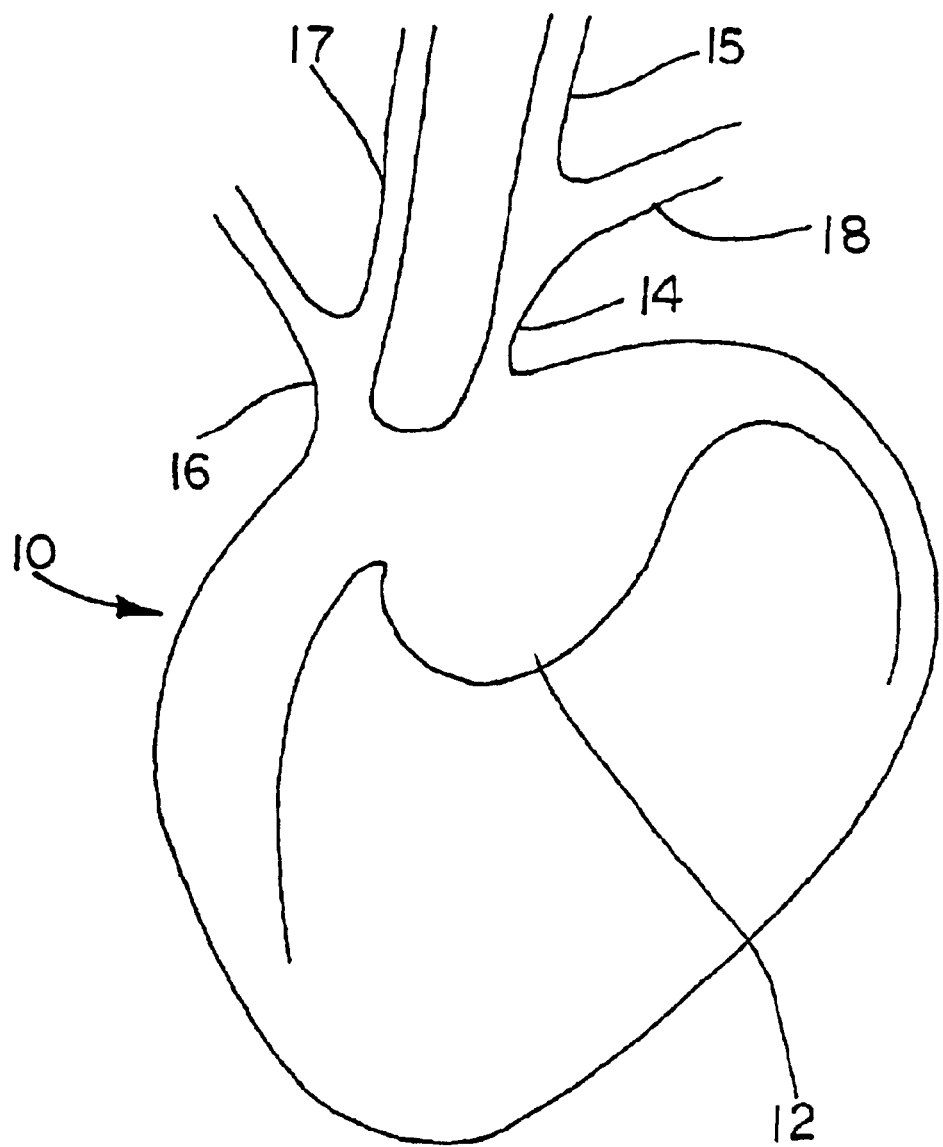
FIG. 1 is a schematic drawing taken from an angiogram of a patient with a large aneurysm of the aortic arch.

Referring now to the drawings, FIG. 1 is a drawing of an aorta 10 having an aneurysm 12 spanning the left brachiocephalic artery 14, the right brachiocephalic artery 16, and the left subclavian artery 18. The right subclavian artery 19 is also shown. Also shown are the left and right common carotid arteries 15, 17, respectively.

Figure 2:
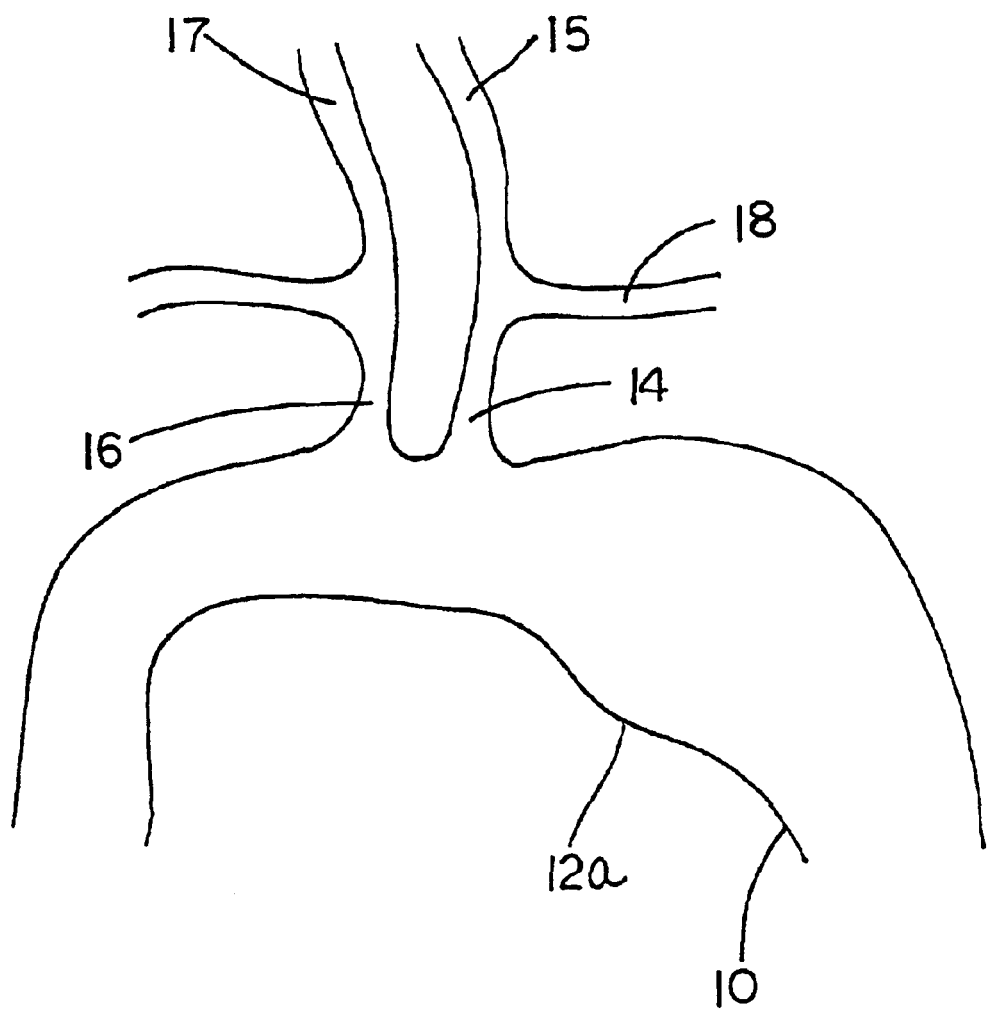
FIG. 2 is a schematic representation of a proximal descending thoracic aortic aneurysm, and further showing the left subclavian artery transposed to the left common carotid artery.

Referring now to FIG. 2, the aorta 10 is shown in which an aneurysm 12a is a descending thoracic aortic aneurysm. As is also shown in FIG. 2, the left subclavian artery 18 has been surgically transposed to the left common carotid artery 15. The impact of the transposition of the left subclavian artery 18 to the left common carotid artery 15 will be discussed in greater detail below.

Figure 3:
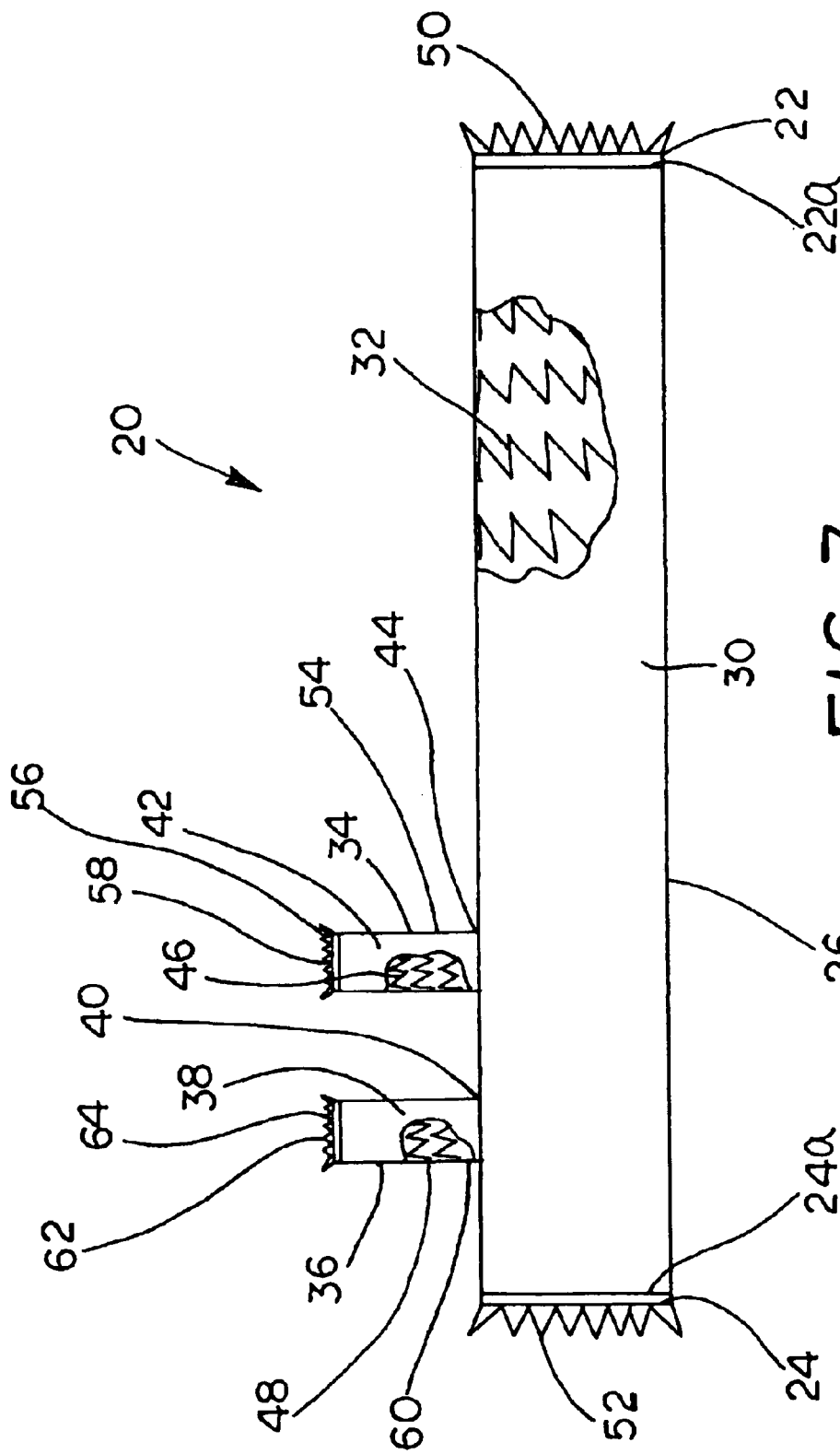
FIG. 3 is an elevational view of a branched aortic arch stent-graft assembled in accordance with the teachings of the present invention.

Referring now to FIG. 3, a stent-graft assembled in accordance with the teachings of the present invention is shown and is generally referred to by the reference numeral 20. In a preferred environment of use, the stent-graft 20 is sized and shaped for insertion into the aortic arch so as to effectively seal off and to treat the aneurysm 12 or 12a illustrated in FIGS. 1 or 2 respectively. Those skilled in the art will understand that other environments of use may be contemplated. The stent-graft 20 includes a distal end 22, a proximal end 24, and a main body 26 extending between the distal end 22 and the proximal end 24. It will be appreciated that the main body 26 is generally circular in cross-section so as to define a central lumen 28 which provides a flow path for blood flowing through the aorta 10. The main body 26 of the stent-graft 20 includes a vascular graft 30 and an expandable stent 32 (the stent 32 being shown by a partial cut-away of the main body 26).

According to the disclosed example, the vascular graft 30 will preferably be constructed of Dacron®, Gore-Tex®, or any other suitable vascular graft material as would be known to those of skill in the art. The stent 32 is preferably constructed of a wire mesh material, and still preferably is constructed of stainless steel or other conventional stent construction, although Nitinol® also may prove suitable. In the disclosed example, the stent 32 is shown in a Z-shaped configuration, although other configurations such as, for example, a criss-crossing configuration, may also prove suitable. Other materials and structures for the stent 32 may be used.

In accordance with the disclosed example, the graft 30 and the stent 32 are joined to each other with the graft 30 surrounding the stent 32. The graft 30 and the stent 32 are preferably secured together so as to form a single integral unit.

The main body 26 of the stent-graft 20 includes a left branch 34 and a right branch 36. The left branch 34 includes a vascular graft 38 which is suitably joined to the vascular graft 30 along a generally circular interface 40. Similarly, the right branch includes a vascular graft 42, which is suitably joined to the vascular graft 30 of the main body 26 along a generally circular interface 44. The left branch 34 also includes an internal stent 46, while the right branch 36 includes an internal stent 48 (the stents 46 and 48 being shown in partial cut away). The stents 46 and 48 may be similar to the stent 32 in construction and, in the disclosed example are formed in a Z-shaped configuration, although other configurations such as, for example, a criss-crossing configuration, may also prove suitable. Other materials and structures for the stents 46 and 48 may be used. It will be appreciated that the stent 32 of the main body 26 will be provided with suitable apertures (not shown) adjacent the locations of the left and right branches 34, 36, respectively, such that a flow passage 34a, 36a is defined in each of the left and right branches 34, 36, respectively, with the flow passages 34a, 36a being in fluid communication with the central lumen 28. Preferably, the stents 46 and 48 are expandable independently of the stent 32 in the main body 26 as will be explained in greater detail below. Also, it will be appreciated that the stent-graft 20 as shown in FIG. 3 illustrates each of the main body 26 and the left and right branches 34, 36 in an expanded or deployed configuration.

In accordance with the disclosed example, each of the distal end 22 and the proximal end 24 may be provided with a radio-opaque marker 22a, 24a, respectively, thus enabling the location of the stent-graft 20 within the aorta 10 to be determined using conventional diagnostic techniques such as, for example, X-rays, MRI, or CAT scan. Still preferably, the stent 32 includes an exposed portion 50 adjacent the distal end 22, and also includes an exposed portion 52 adjacent the proximal end 24 of the main body 26. It will be appreciated that the exposed portions 50, 52 will generally define distal and proximal sealing zones respectively.

The left branch 34 includes a base 54 generally adjacent the interface 44 with the main body 26, and also includes a free end 56 having an exposed portion 58 of the stent 46. Similarly, the right branch 36 includes a base 60 generally adjacent the circular interface 44 with the main body 26, and also includes a free end 62 having an exposed portion 64 of the stent 48. The exposed portions 58, 64 of the left and right branches 34, 36, respectively, will define sealing zones within their respective vessels, which in the disclosed example are the left brachiocephalic artery 14 and the right brachiocephalic artery 16, respectively.

Figure 4:
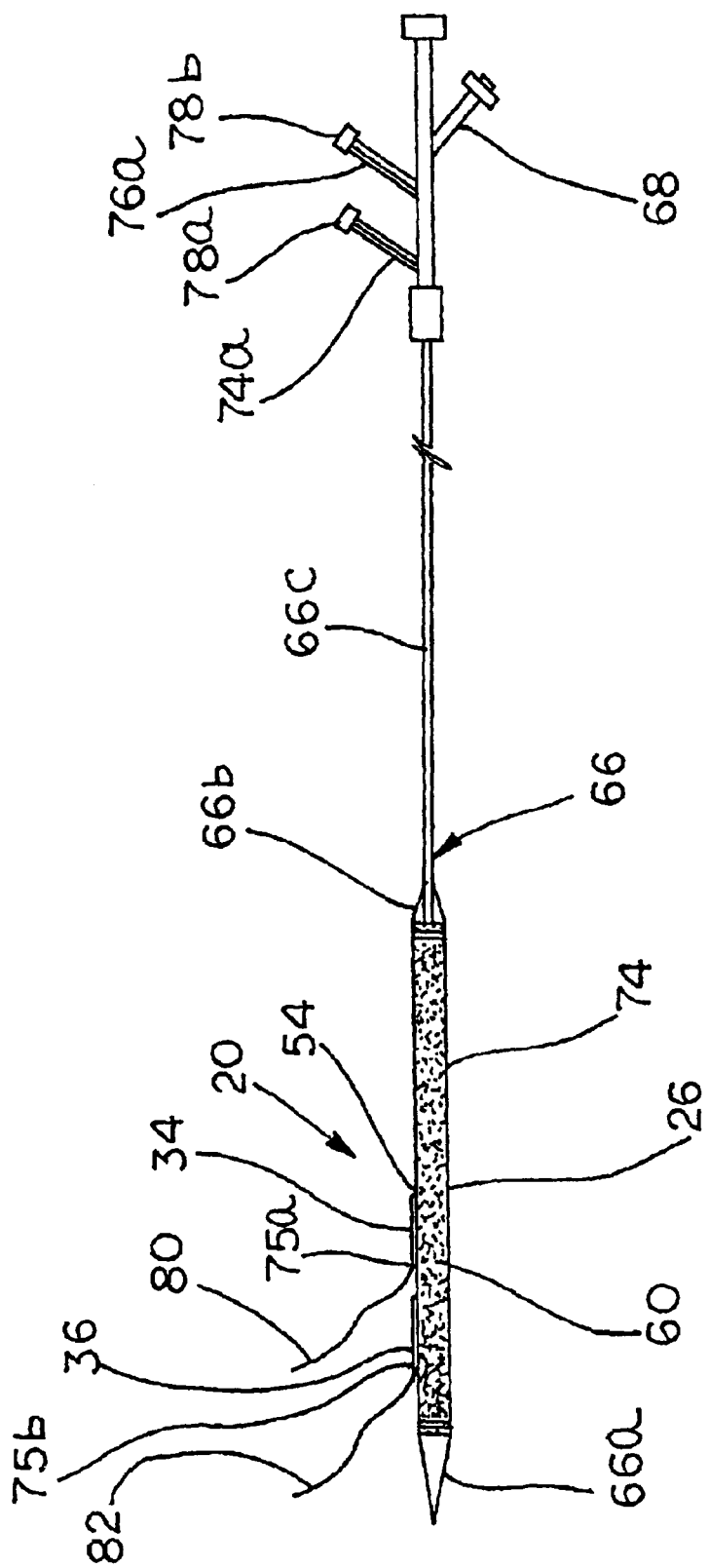
FIG. 4 is an elevational view of the branched aortic arch stent-graft of FIG. 3 shown mounted on a delivery catheter.

Referring now to FIG. 4, the stent-graft 20 is shown therein attached to a four-lumen delivery catheter 66. The delivery catheter 66 includes a proximal taper tip 66a, a distal taper tip 66b, and a shaft 66c. According to the disclosed example, the main lumen runs the entire length of the delivery catheter 66, and accepts a 0.035 inch wire. A flushing side arm 68 connects to the main lumen.

When the stent-graft 20 is disposed on the delivery catheter 66 as shown in FIG. 4, it will be appreciated that the main body 26 as well as the left and right branches 34, 36 are in their narrowed undeployed configuration. Further, it will be appreciated that the left and right branches 34, 36 are generally folded along their respective bases 54, 60, such that the left and right branches 34, 36 are disposed in a folded position lying generally adjacent to the main body 26 of the stent-graft 20.

Figure 5:
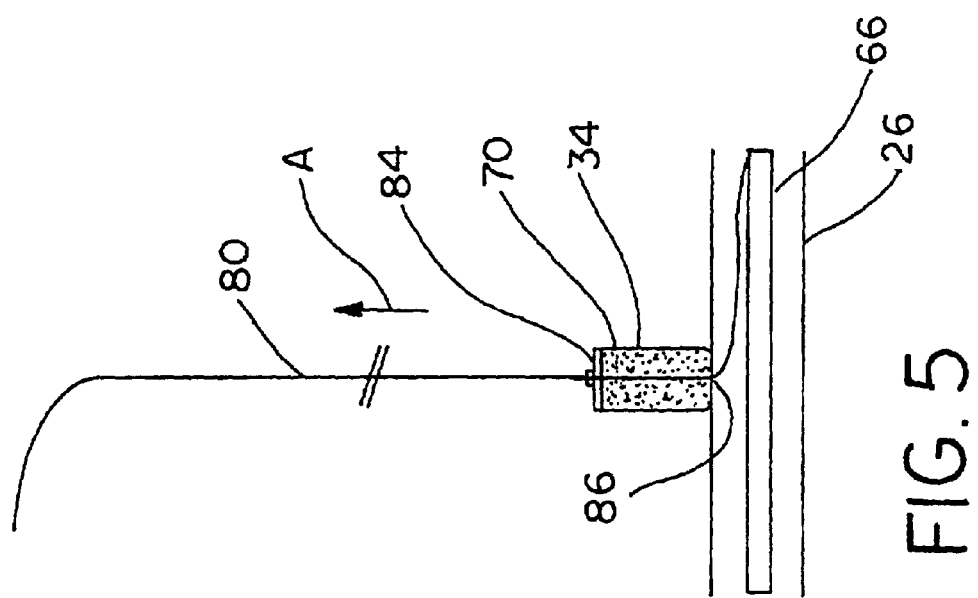
FIG. 5 is an enlarged fragmentary elevational view of a side branch deployment mechanism.
Figure 10:
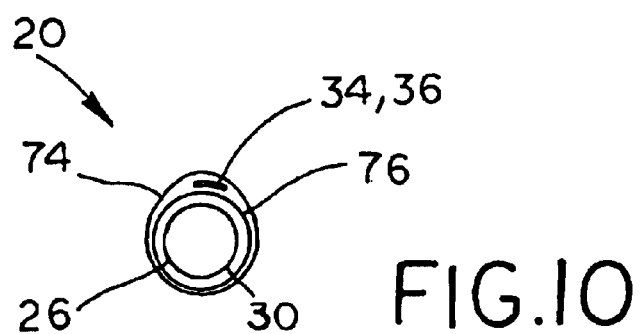
FIG. 10 is a cross-sectional view of the inner and outer sheaths in place over the stent-graft.

When the left and right branches 34, 36 are disposed as shown in FIG. 4, each of the left and right branches 34, 36 are maintained in a narrowed undeployed configuration by a sheath 70, 72, respectively (see FIGS. 5 and 10). Preferably, the stent-graft 20 will be provided with an outer sheath 74 which extends along the main body 26 of the stent-graft 20, and which constrains the left and right branches 34, 36 in the folded position shown. The stent-graft 20 is also provided with an inner sheath 76 (obscured by the outer sheath 74 in FIG. 4 but shown in FIG. 10) which constrains the main body 26 of the stent-graft in the narrowed undeployed configuration of FIG. 4. The sheaths 70, 72, 74, and 76 may be constructed of the same material as is used in the construction of the graft, although other suitable materials may be used.

The outer sheath 74 and the inner sheath 76 are preferably released using deployment lines 74a, 76a, respectively, which run through one of the lumens of the delivery catheter 66. The deployment lines 74a, 76a will preferably extend to a pair of knobs 78a, 78b, which are connected to the lines 74a, 76a respectively. Using the knobs 78a, 78b and the lines 74a, of 76a, the outer sheath 74 and the inner sheath 76 may be released in a known manner. As will be explained in greater detail below, the outer sheath 74 is released first, which thus permits the left branch 34 and the right branch 36 to shift from the folded position of FIG. 4 to the unfolded position shown in FIG. 5 such that the left and right branches 34 and 36 may be positioned in the left and right brachiocephalic arteries 14, 16 in a manner that will be explained in greater detail below.

The stent-graft 20 includes a left pull wire 80 and a right pull wire 82 when the stent-graft 20 is disposed on the delivery catheter 66 as shown in FIG. 4. The left pull wire extends into the left branch 34 and into one of the available lumens on the delivery catheter 66, while the right pull wire 82 extends into the right branch and into another available lumen on the delivery catheter 66. Each of the left and right pull wires 80, 82 include an exposed portion 80a, 82a, respectively, which exposed portions protrude slightly from the free end of their respective branches. Preferably, the left and right pull wires 80, 82 are 0.018 inch wires which may run the length of the shaft 66c but which are not attached to the delivery catheter 66. The wires 80, 82 can only be fully withdrawn from the delivery catheter 66 after the outer sheath 74 and the inner sheath 76 have been removed as described above. In the disclosed example this helps to prevent premature deployment of the left and right branches 34, 36. The outer sheath 74 may be provided with suitable apertures 75a, 75b, such that the exposed portions 80a, 82a are accessible.

Preferably, the inner and outer sheaths 74, 76 will be bound to the main body 26 of the stent-graft 20. Thus, upon release of the sheaths 74, 76 using the appropriate knobs and wires, the sheaths 74, 76 will remain permanently between the main body 26 and the wall of the aneurysm.

Referring now to FIG. 5, the left branch 34 is shown therein in the unfolded configuration extending away from the main body of the stent-graft 20. Although the left branch 34 is shown, it will be understood that following description will apply equally to the right branch 36, and thus for the sake of brevity only the operation and deployment of the left branch 34 will be described in detail. It will be understood that the operation and deployment of the right branch 36 is substantially identical. The left branch 34 is disposed in the narrowed undeployed configuration still constrained by the sheath 70. It will be noted that the main body 26 of the stent-graft 20 is already in the expanded deployed configuration, thus indicating that both the outer sheath 74 and the inner sheath 76 have already been released. The sheath 70 of the left branch 34 is provided with a deployment catch 84, while the left pull wire 80 is provided with a deployment button 86. Preferably, the deployment button 86 will have a generally conical configuration. In response to movement of the left pull wire 80 in a direction away from the main body 26 of the stent-graft 20 (which direction is indicated by the reference arrow A), the left pull wire 80 may be used to remove the sheath 70 of the left branch 34 by virtue of the fact that the deployment button 86 will engage the deployment catch 84 as the left pull wire 80 is being drawn in the indicated direction. With the removal of the sheath 70, the left branch 34 is free to expand from the narrowed configuration illustrated in FIG. 8, to the expanded deployed configuration illustrated in FIG. 9. Again, it will be understood that the operation and deployment of the right branch 36, including the removal of the sheath 72 of the right branch 76, is identical, with the right branch 36 and its corresponding right pull wire 82 being provided with the appropriate catch 84 and deployment button 86 as necessary.

Figure 6:
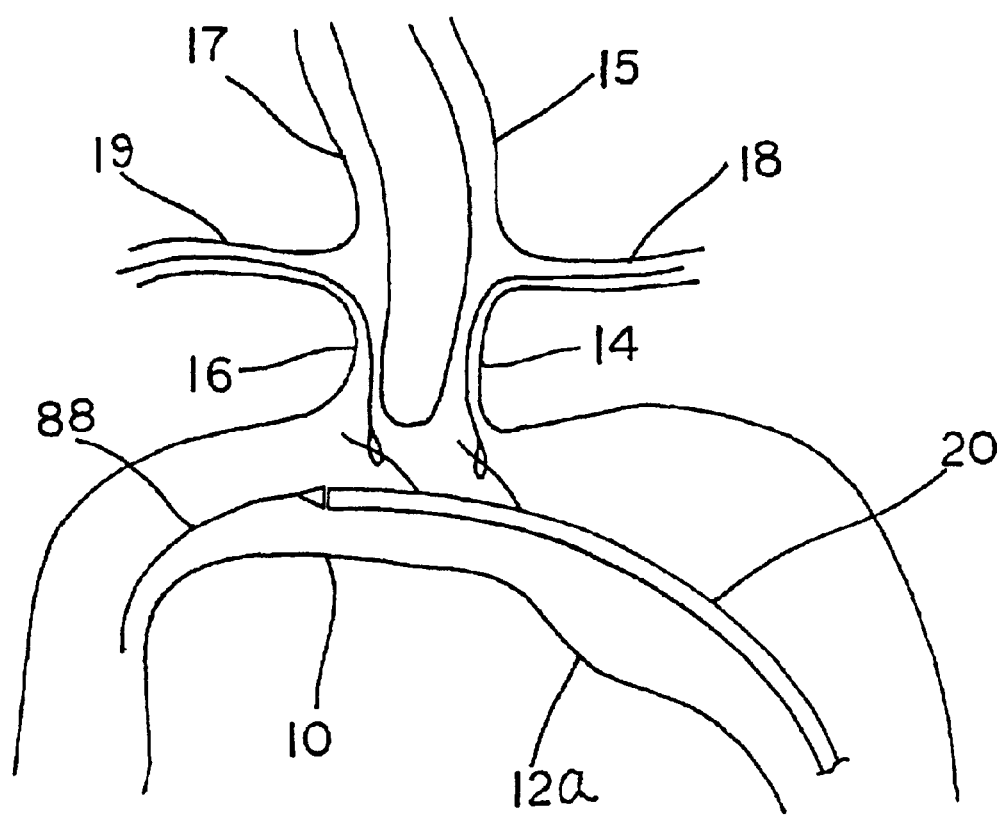
FIG. 6 is a schematic illustration similar to FIG. 2 and illustrating the snaring of the proximal (right) and distal (left) pull wires.
Figure 7:
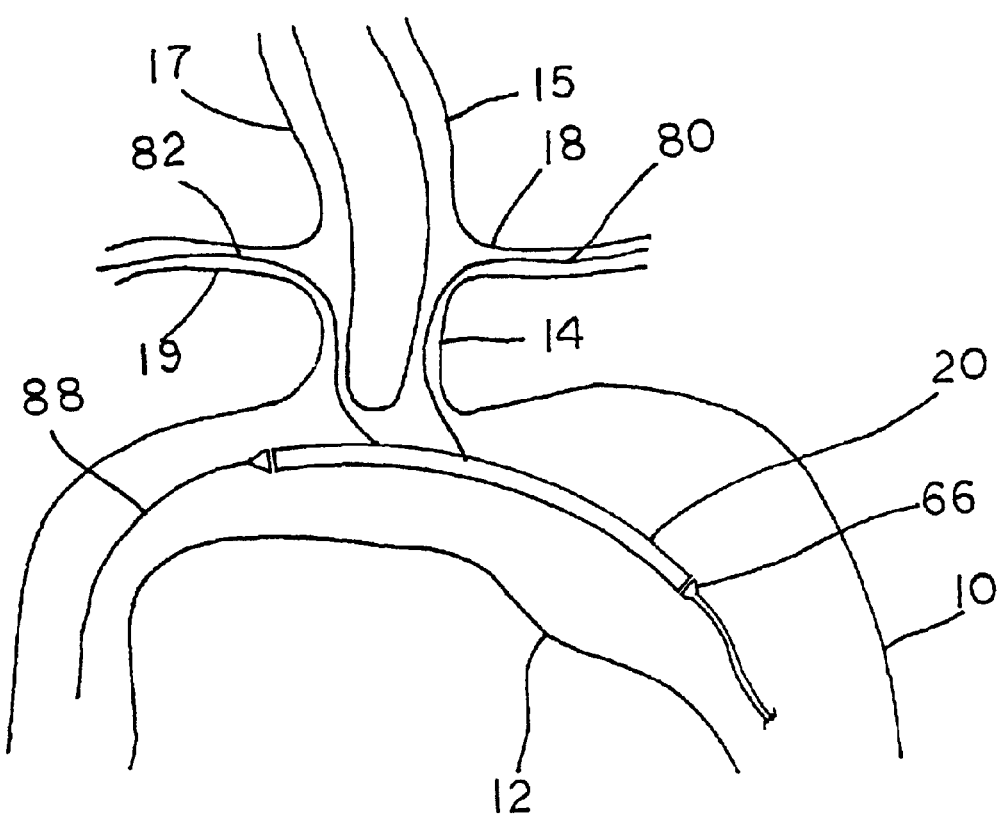
FIG. 7 is a schematic representation similar to FIGS. 2 and 6 and illustrating the stent-graft assembly of the present invention being advanced across the aneurysm.

Referring now to FIG. 6, the stent-graft 20 is shown therein attached to the delivery catheter 66 and being inserted into the aortic arch guided by a main guide wire 88 in a known manner. It will be noted that the exposed portions 80a, 82a of the left and right pull wires 80, 82, respectively, are positioned and arranged to be engaged by left and right snares 90, 92, respectively. Preferably the snares 90, 92 are goose-neck snares. In a preferred method of deployment of the stent-graft 20, the left snare is inserted through the left brachiocephalic artery 14 via the transposed left subclavian artery and via the left brachial artery, while the right snare 92 is inserted through the right brachiocephalic artery 16 via the right subclavian artery 19. It will be noted that when the stent-graft 20 is being inserted into the aortic arch as shown in FIG. 6, the sheaths 70, 72 constrain the left and right branches 34, 36 in their respective narrowed and undeployed configurations, while at the same time the inner sheath 76 constrains the main body 26 in the narrowed undeployed configuration and the outer sheath 74 constrains each of the left and right branches 34, 36 in the folded position generally adjacent the main body 26. As shown in FIG. 7, as the stent-graft 20 is being advanced into position in the aortic arch, after the left and right pull wires 80, 82 have been snared by the respective snares 90, 92, traction may be maintained on the pull wires. Upon release of the outer sheath 74, the left and right branches 34, 36 are then free to be pulled under tension into the respective left and right common carotid arteries 14, 16. It will be appreciated that, upon release of the outer sheath 74, the left and right branches 34, 36 are free to shift from the folded position disposed adjacent the main body 26 of the stent-graft 20 to the position generally shown in FIG. 5.

Figure 8:
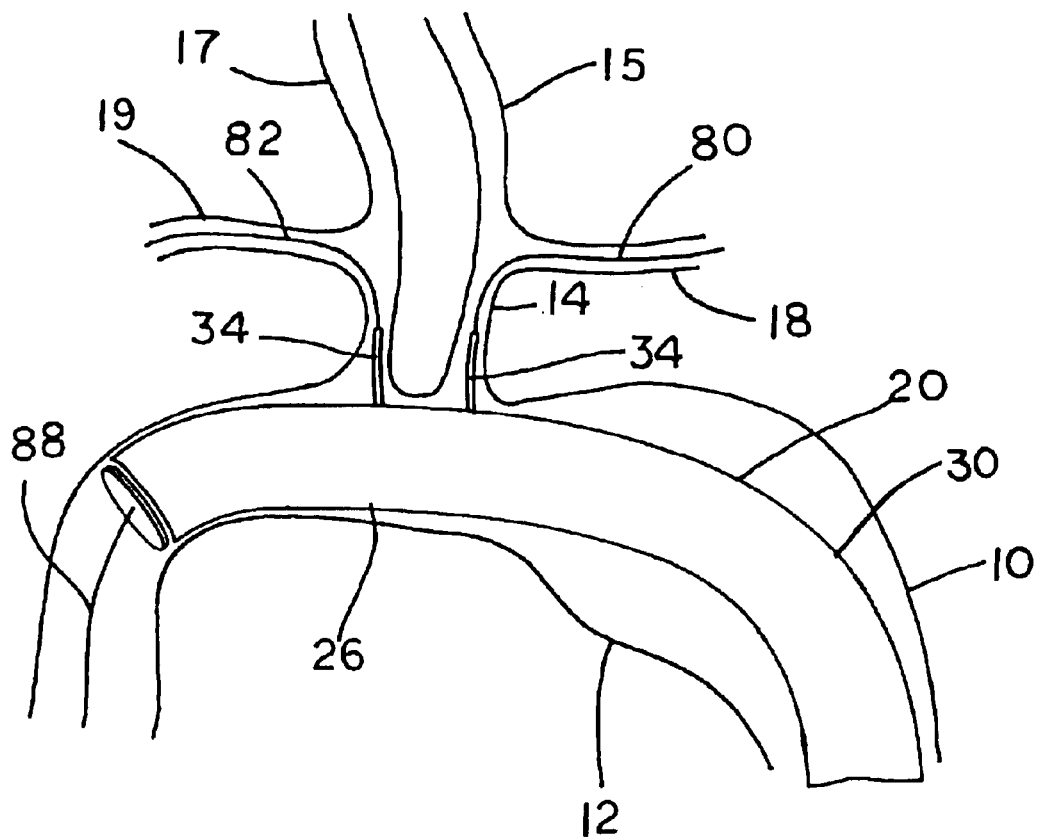
FIG. 8 is a schematic representation similar to FIG. 7 but with the main body of the stent-graft shown in an expanded deployed configuration and with the side branches disposed in their respective vessels prior to deployment.

Referring now to FIG. 8, the stent-graft 20 is shown in proper position within the aorta 10 with the left and right branches 34, 36 appropriately positioned in their corresponding carotid arteries. Diagnostic imaging of the type commonly employed in the art may be employed to confirm proper positioning of the stent-graft 20 using the radio-opaque markers 22a, 24a. In FIG. 8, it will be appreciated that the outer sheath 74 has already been released (thus permitting the left and right branches to be positioned as shown), and the inner sheath 76 has also been released. Upon release of the inner sheath 76, the main body 26 of the stent-graft 20 is free to expand to the expanded deployed configuration shown. In the event that the stent 32 is manufactured to be self-expanding, the main body 26 will expand to the configuration shown automatically upon release of the inner sheath 76. Alternatively, it will be understood that the stent may be expanded using a balloon of the type commonly employed in the art. The left and right pull wires 80, 82 are then withdrawn out of the delivery catheter 66 in the direction indicated by the reference arrow A, thus enabling the sheath 70 of the left branch 34 and the sheath 72 of the right branch 36 to be removed. Upon removal of the sheaths from the left and right branches 34, 36, the left branch and the right branch will automatically expand to their expanded deployed configurations. Again, in the event that the stents in the left and right branches are not self-expanding, the left and right branches 34, 36 may be expanded using a balloon in a known manner.

Figure 9:
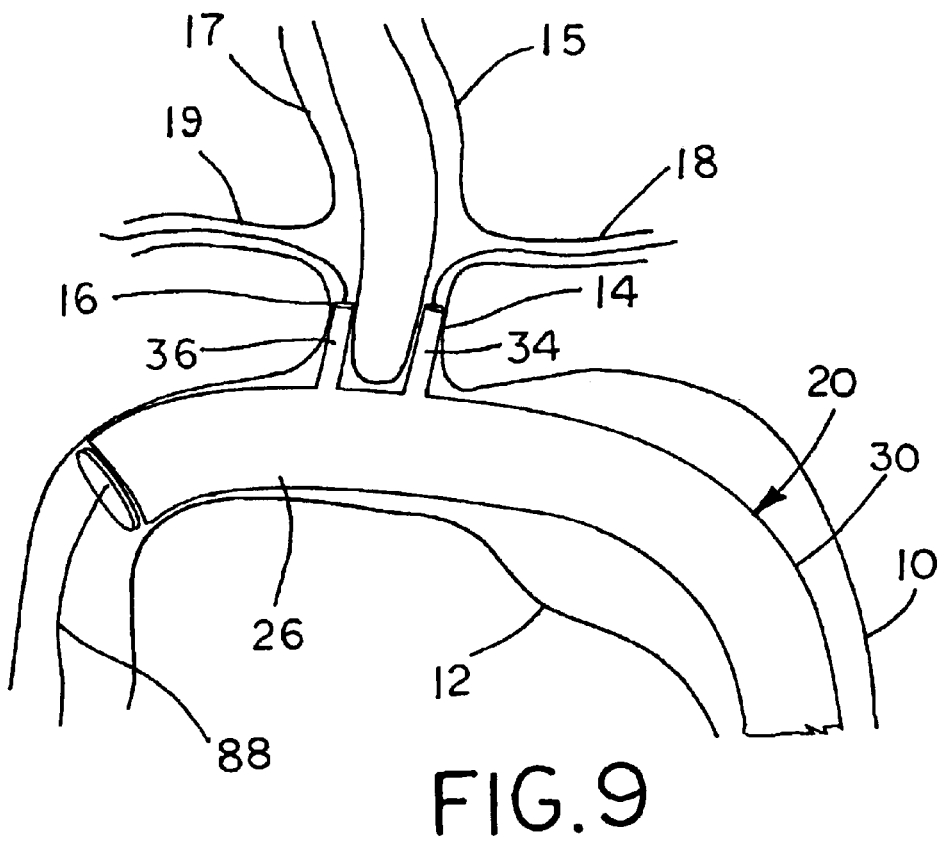
FIG. 9 is a schematic representation similar to FIG. 8 and illustrating the main body of the stent-graft and the side branches of the stent-graft in their expanded deployed configurations.

Referring now to FIG. 9, the stent-graft 20 is shown therein in a fully deployed configuration. The deployment catheter 66 may be retracted back over the main guide wire, allowing for balloon catheters to oppose the stent-graft 20 and its branches 34, 36 to their corresponding vessel walls.

In accordance with the disclosed example, a two-sided branched stent-graft allows patients with thoracic aneurysmal disease to be treated using a less-invasive approach than conventional open surgery. Furthermore, the disclosed device and method could allow patients to be treated who are declined conventional surgery because of prohibitive operative risk. In addition, the device may be applicable to treat patients with thoracic aortic transection as a result of trauma, or patients with acute dissection enabling a central endovascular repair of the thoracic aorta.

In the foregoing, the construction of a side-branched stent-graft has been described. The device is designed to straddle the origins of the brachiocephalic vessels so that the proximal landing zone is located in the distal ascending aorta, and the distal landing zone in the descending aorta. To minimize the complexity of cannulating three brachiocephalic vessels to maintain antegrade blood flow, transposition of the left subclavian artery 18 to the left common carotid artery 15 is performed prior to aortic endovascular repair (FIGS. 2 and 6–9). This allows the use of a stent-graft 20 with only 2 side-branches. The safety and durability of subclavian to carotid artery transposition has been described elsewhere.

What is claimed:

1. A device for placement in the aortic arch and spanning the left brachiocephalic artery and the right brachiocephalic artery, the device comprising:

a graft, the graft having a main body sized for insertion in the aortic arch and defining a central lumen;

the graft having a left branch and a right branch attached to the main body and arranged for flow communication with the central lumen, each of the main body, the left branch and the right branch including a stent and shiftable between a narrowed undeployed configuration and an expanded deployed configuration;

the left branch including a sheath arranged to constrain the left branch in the undeployed configuration, the left branch arranged to be pulled into the left brachiocephalic artery exclusively under tension by a left pull wire;

the right branch including a sheath arranged to constrain the right branch in the undeployed configuration, the right branch arranged to be pulled into the right brachiocephalic artery exclusively under tension by a right pull wire;

an inner sheath, the inner sheath arranged to constrain the main body of the graft in the undeployed configuration; and an outer sheath, the outer sheath arranged to constrain each of the left branch and the right branch in a folded position generally adjacent the main body when each of the left branch and the right branch is in the undeployed configuration.

2. The device of claim 1, wherein the sheath of the left branch and the sheath of the right branch are arranged for removal exclusively under tension by the left pull wire and the right pull wire respectively.

3. The device of claim 1, wherein the main body includes a proximal end and a distal end, and wherein the stent of the main body is sized to include an exposed portion extending beyond the proximal end and the distal end of the main body, each exposed portion forming a sealing zone.

4. The device of claim 1, wherein each of the left pull wire and the right pull wire includes a catch arranged to engage and remove the sheath of the left branch and the right branch, respectively, thereby permitting the left branch and the right branch to shift to the deployed configuration.

5. The device of claim 1, wherein the stent of the main body includes a left aperture adjacent the left branch and a right aperture adjacent the right branch.

6. The device of claim 1, wherein the stent of the main body and the stent of the left and right branches are formed of self-expanding stainless steel.

7. A device for placement in the aortic arch and spanning the left brachiocephalic artery and the right brachiocephalic artery, the device comprising:

a graft, the graft having a main body sized for insertion in the aortic arch and defining a central lumen;

the graft having a left branch and a right branch attached to the main body and arranged for flow communication with the central lumen, each of the main body, the left branch and the right branch including a stent and shiftable between a narrowed undeployed configuration and an expanded deployed configuration;

the left branch including a sheath arranged to constrain the left branch in the undeployed configuration, the left branch arranged to be pulled into the left brachiocephalic artery exclusively under tension by a left pull wire;

the right branch including a sheath arranged to constrain the right branch in the undeployed configuration, the right branch arranged to be pulled into the right brachiocephalic artery exclusively under tension by a right pull wire;

an inner sheath, the inner sheath arranged to constrain the main body of the graft in the undeployed configuration;

an outer sheath, the outer sheath arranged to constrain each of the left branch and the right branch in a folded position generally adjacent the main body when each of the left branch and the right branch is in the undeployed configuration; and wherein the left pull wire is sized to extend into the left brachiocephalic artery and the right pull wire is sized to extend into the right brachiocephalic artery, each of the left and right pull wires arranged for engagement by a corresponding snare wire.

8. The device of claim 7, wherein each of the left pull wire and the right pull wire is arranged to be fully removed from the device in response to pulling forces provided by the corresponding snares, each pull wire further including a catch arranged to engage and remove the sheath of the left branch and the right branch, respectively, thereby permitting the left branch and the right branch to shift to the deployed configuration.

9. The device of claim 1, wherein the main body, the left and right branches, and the pull wires are arranged for insertion into the aortic arch using a multi-lumen delivery catheter.

10. A device for placement in the aortic arch and spanning the left brachiocephalic artery and the right brachiocephalic artery, the device comprising:

a graft, the graft having a main body sized for insertion in the aortic arch and defining a central lumen;

the graft having a left branch and a right branch attached to the main body and arranged for flow communication with the central lumen, each of the main body, the left branch and the right branch including a stent and shiftable between a narrowed undeployed configuration and an expanded deployed configuration;

the left branch including a sheath arranged to constrain the left branch in the undeployed configuration, the left branch arranged to be pulled into the left brachiocephalic artery exclusively under tension by a left pull wire;

the right branch including a sheath arranged to constrain the right branch in the undeployed configuration, the right branch arranged to be pulled into the right brachiocephalic artery exclusively under tension by a right pull wire;

an inner sheath, the inner sheath arranged to constrain the main body of the graft in the undeployed configuration;

an outer sheath, the outer sheath arranged to constrain each of the left branch and the right branch in a folded position generally adjacent the main body when each of the left branch and the right branch is in the undeployed configuration; and wherein the device is arranged for delivery into the aorta using a multi-lumen catheter, and wherein each of the left and right pull wires are arranged to exit the delivery catheter exclusively through the left and right branches, and further wherein each of the inner and outer sheaths are arranged for release using sheath pull wires extending through the catheter.

11. The device of claim 1, wherein at least one of the main stent, the left stent and the right stent is arranged to automatically shift the corresponding graft to the deployed position upon removal of the corresponding sheath.

12. A device for placement in the aortic arch, the device comprising:

a graft, the graft having a main body sized for insertion in the aortic arch and spanning the left brachiocephalic artery and the right brachiocephalic artery, the main body defining a central lumen, the main body including a stent and shiftable between a narrowed undeployed configuration and an expanded deployed configuration;

the graft having a left branch and a right branch attached to the main body and arranged for flow communication with the central lumen, each of the left branch and the right branch including a stent and shiftable between a narrowed undeployed configuration and an expanded deployed configuration, each of the left branch and the right branch further including a sheath, the sheath of the left branch and the sheath of the right branch arranged to constrain the corresponding branch in the undeployed configuration, the left branch arranged to be pulled into the left brachiocephalic artery exclusively under tension by a left pull wire, the right branch arranged to be pulled into the right brachiocephalic artery exclusively under tension by a right pull wire;

an inner sheath, the inner sheath arranged to constrain the main body of the graft in the undeployed configuration; and an outer sheath, the outer sheath arranged to constrain each of the left branch and the right branch in a folded position generally adjacent the main body when each of the left branch and the right branch is in the undeployed configuration.

13. A device for placement in the aortic arch and spanning the left brachiocephalic artery and the right brachiocephalic artery, the device comprising:

a graft, the graft having a main body sized for insertion in the aortic arch and defining a central lumen, the main body including a stent and shiftable between a narrowed undeployed configuration and an expanded deployed configuration;

the graft having a left branch and a right branch attached to the main body and arranged for flow communication with the central lumen, each of the left branch and the right branch including a stent and shiftable between a narrowed undeployed configuration and an expanded deployed configuration, each of the left branch and the right branch further including a sheath, the sheath of the left branch and the sheath of the right branch arranged to constrain the corresponding branch in the undeployed configuration, the left branch arranged to be pulled into the left brachiocephalic artery exclusively under tension by a left pull wire, the right branch arranged to be pulled into the right brachiocephalic artery exclusively under tension by a right pull wire;

an inner sheath, the inner sheath arranged to constrain the main body of the graft in the undeployed configuration;

an outer sheath, the outer sheath arranged to constrain each of the left branch and the right branch in a folded position generally adjacent the main body when each of the left branch and the right branch is in the undeployed configuration; and wherein the left pull wire is sized to extend into the left brachiocephalic artery and the right pull wire is sized to extend into the right brachiocephalic artery, each of the left and right pull wires arranged for withdrawal exclusively under tension through a free end of the corresponding branch.

14. The device of claim 13, wherein the left pull wire and the right pull wire each includes a catch arranged to remove the corresponding sheath in response to withdrawal of the pull wires, each of the left and right branches arranged to automatically shift to the deployed configuration in response to removal of the corresponding sheath.

15. The device of claim 13, wherein the left pull wire and the right pull wire each includes a catch arranged to remove the corresponding sheath in response to withdrawal of the pull wires, the left pull wire arranged to exit the aorta via the left brachiocephalic artery and the right pull wire arranged to exit the aorta through the right brachiocephalic artery.

16. The device of claim 12, wherein the stent of the main body and the stent of the left and right branches are formed of self-expanding stainless steel.

17. The device of claim 12, wherein the main body includes a proximal end and a distal end, and wherein the stent of the main body is sized to include an exposed portion extending beyond the proximal end and the distal end of the main body, each exposed portion forming a sealing zone.

18. The device of claim 12, wherein the stent of the main body includes a left aperture adjacent the left branch and a right aperture adjacent the right branch.

19. The device of claim 12, wherein the main body, the left and right branches, and the pull wires are arranged for insertion into the aortic arch using a multi-lumen delivery catheter.

20. A method of repairing an aneurysm in the aortic arch having a left subclavian artery transposed to the left common carotid artery, the method comprising the steps of:

providing a graft, the graft having a main body sized for insertion in the aortic arch and defining a central lumen, the main body including a stent and shiftable between a narrowed undeployed configuration and an expanded deployed configuration;

providing the graft with a left branch and a right branch attached to the main body and arranged for flow communication with the central lumen, each of the left branch and the right branch including a stent and shiftable between a narrowed undeployed configuration and an expanded deployed configuration;

providing a sheath on each of the left branch and the right branch, each sheath arranged to constrain the corresponding branch in the undeployed configuration;

providing an inner sheath to constrain the main body of the graft in the undeployed configuration;

providing an outer sheath arranged to constrain each of the left branch and the right branch in a folded position generally adjacent the main body when each of the left branch and the right branch is in the undeployed configuration;

inserting the graft into the aortic arch with the graft spanning both the left and the right brachiocephalic arteries;

pulling the let branch into the left brachiocephalic artery exclusively under tension by a left pull wire;

pulling the right branch into the right brachiocephalic artery exclusively under tension by a right pull wire; and removing the outer sheath, the inner sheath, and the sheaths constraining the left and right branches.

* * * * *

UNITED STATES PATENT AND TRADEMARK OFFICE
CERTIFICATE OF CORRECTION

PATENT NO. : 6,918,925 B2
DATED : July 19, 2005
INVENTOR(S) : Hassan Tehrani

It is certified that error appears in the above-identified patent and that said Letters Patent is hereby corrected as shown below:

Column 10,
Line 51, please delete "let" and insert instead -- left --.

Signed and Sealed this

Twenty-fifth Day of October, 2005

JON W. DUDAS
*Director of the United States Patent and Trademark Office*